United States Patent [19]
Takagi

[11] Patent Number: 5,616,618
[45] Date of Patent: Apr. 1, 1997

[54] THREO-3-(3,4-DIHYDROXYPHENYL)SERINE ANALGESIC COMPOSITION

[75] Inventor: Hiroshi Takagi, Kyoto, Japan

[73] Assignee: Sumitomo Pharmaceuticals Company, Limited, Osaka, Japan

[21] Appl. No.: 495,480

[22] PCT Filed: Jan. 28, 1994

[86] PCT No.: PCT/JP94/00120

§ 371 Date: Jul. 24, 1995

§ 102(e) Date: Jul. 24, 1995

[87] PCT Pub. No.: WO94/16689

PCT Pub. Date: Aug. 4, 1994

[30] Foreign Application Priority Data

Jan. 29, 1993 [JP] Japan ...................................... 5-034366

[51] Int. Cl.$^6$ .......................... A01N 37/12; A61K 31/195
[52] U.S. Cl. ............................................................. 514/567
[58] Field of Search ............................................... 514/567

[56] References Cited

U.S. PATENT DOCUMENTS

| | | | |
|---|---|---|---|
| 4,529,603 | 7/1985 | Mori et al. | 514/565 |
| 4,647,587 | 3/1987 | Katsube et al. | 514/567 |

FOREIGN PATENT DOCUMENTS

| | | |
|---|---|---|
| 32540 | 9/1974 | Japan . |
| 125630 | 10/1977 | Japan . |
| 67420 | 4/1985 | Japan . |

*Primary Examiner*—Rebecca Cook
*Attorney, Agent, or Firm*—Sughrue, Mion, Zinn, Macpeak & Seas

[57] ABSTRACT

Threo-3-(3,4-dihydroxyphenyl)serine exhibits an analgesic effect against acute pains and chronic or continuous pains. Therefore, threo-3-(3,4-dihydroxyphenyl)serine is effective for the treatment of diseases with pains such as postoperative pain, headache, migraine, pains accompanied by rheumatism, post-herpes neuralgia, cancerous pain, pains associated with cervico-omo-brachial syndrome, shoulder periarthritis, spinal distortion, and spondylosis deformans.

4 Claims, 5 Drawing Sheets

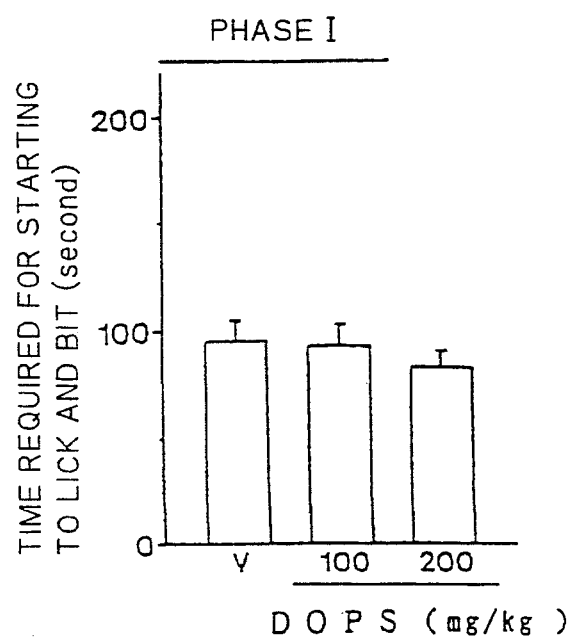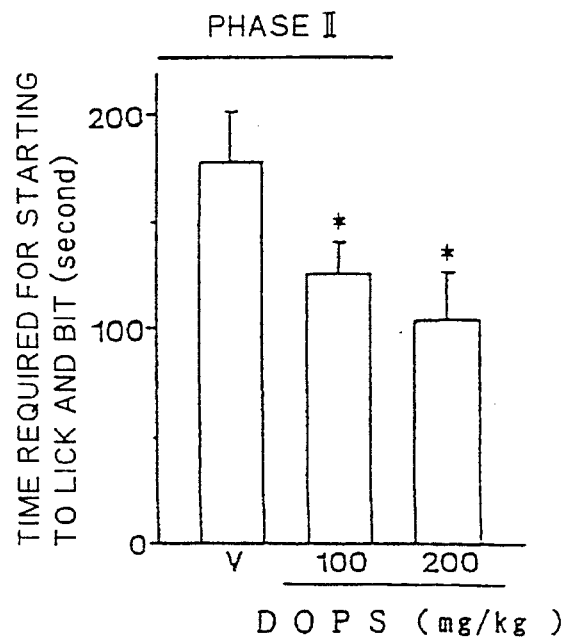

TAIL FLICK TEST

KAOLIN-INDUCED WRITHING TEST

EFFECT OF PHENTOLAMINE, i.c.v.

EFFECT OF PHENTOLAMINE, i.th.

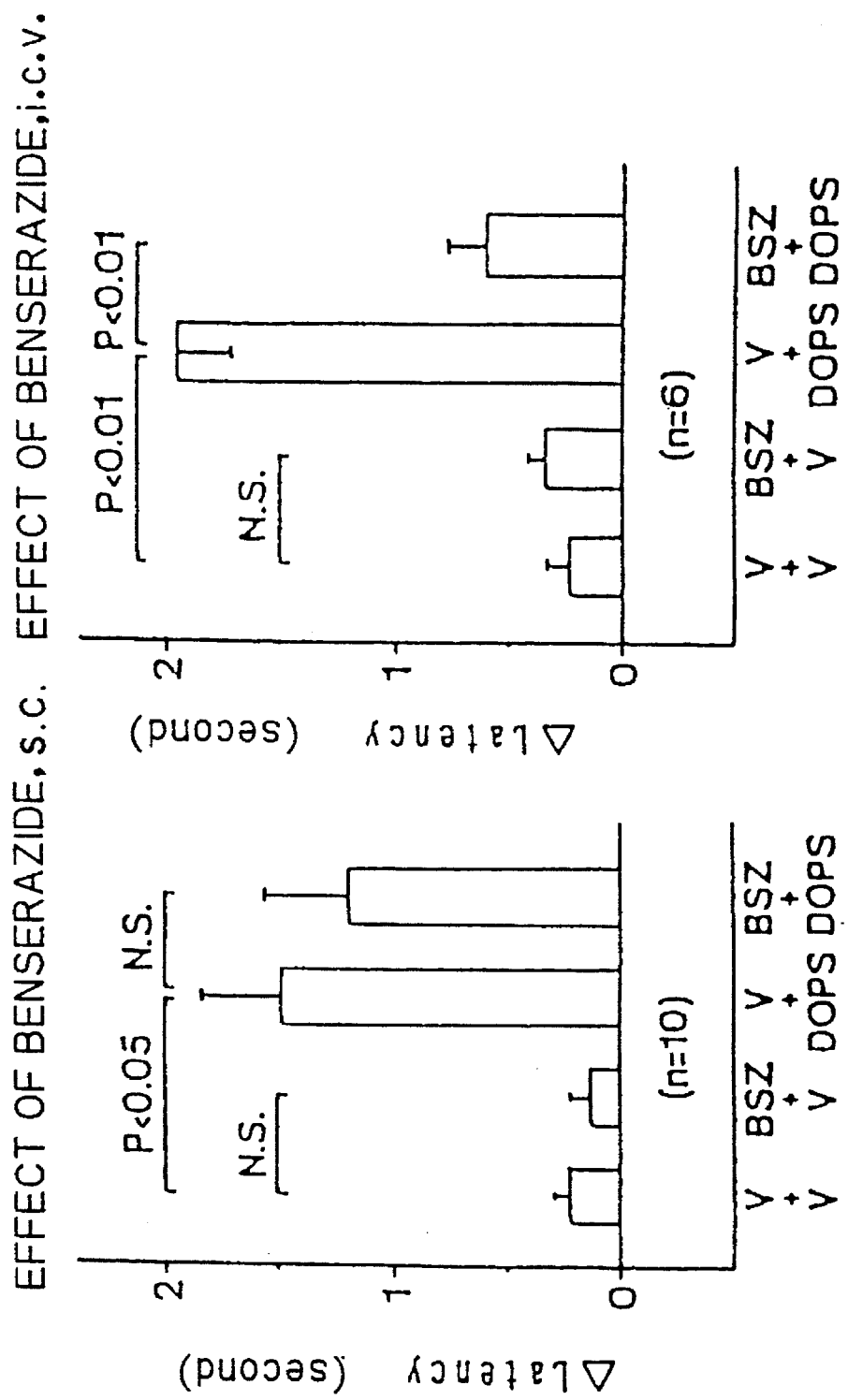

THREO-3-(3,4-DIHYDROXYPHENYL)SERINE ANALGESIC COMPOSITION

This application is a 371 of PCT/JP94/00120.

TECHNICAL FIELD

The present invention relates to a medical use of threo-3-(3,4-dihydroxyphenyl)serine (hereinafter abbreviated as threo-DOPS). More particularly, the present invention relates to a medical use of threo-DOPS as an analgesic drug, especially in the treatment of acute and chronic pains or continuous pains.

BACKGROUND ART

Analgesic drugs are roughly classified into a narcotic type and a non-narcotic type. The latter type of analgesics have been widely employed for clinical use due to their safety and easy manipulation.

In terms of clinical classification, there are two types of pains, i.e., acute pains and chronic or continuous pains. Acute pains are induced by specific causes such as wound and inflammation. Conventional analgesics have all been developed and clinically used for acute pains. On the other hand, chronic pains involve continuous pains over more than 6 months to a few years even after wounds causing acute pains have been healed. For such chronic pains, conventional analgesics are not always effective. A variety of drugs such as antidepressants and antispasmodics are applied to relieve chronic pains but there has been no decisive drug so far [Hiroshi Takagi, "Kyuseitsu-oyobi-Manseitsuno-Yakuri (Pharmacology of acute and chronic pains)", Nihon Ishikai Zasshi, Vol. 104, No. 1, pages 37–41, 1990].

Therefore, an object of the present invention is to provide an analgesic drug which is different from known analgesics in the action mechanism and is effective not only for acute pains but also for chronic pains.

DISCLOSURE OF INVENTION

The present inventors have made extensive studies to achieve the foregoing object. As a result, it has been discovered that a pharmaceutical composition comprising threo-DOPS as an effective ingredient exhibits an analgesic activity to relieve chronic or continuous pain as well as acute pain. The present invention has thus been accomplished.

That is, the present invention relates to an analgesic composition comprising as an effective ingredient threo-DOPS or a pharmaceutically acceptable acid addition salt thereof.

The present invention also relates to a method for the treatment of diseases with pains which comprises administering to human an effective dose of threo-DOPS or a pharmaceutically acceptable acid addition salt thereof.

The present invention further relates to use of threo-DOPS or a pharmaceutically acceptable acid addition salt thereof in the production of an analgesic composition.

BRIEF DESCRIPTION OF DRAWINGS

FIG. 3 shows the results of the analgesic effect of L-threo-DOPS assessed by the formalin-induced encroachment test.

FIG. 6 shows the results of decarboxylase inhibitor, benserazide, on the analgesic effect of L-threo-DOPS assessed by the tail flick method.

BEST MODE FOR CARRYING OUT THE INVENTION

Figure 1A:
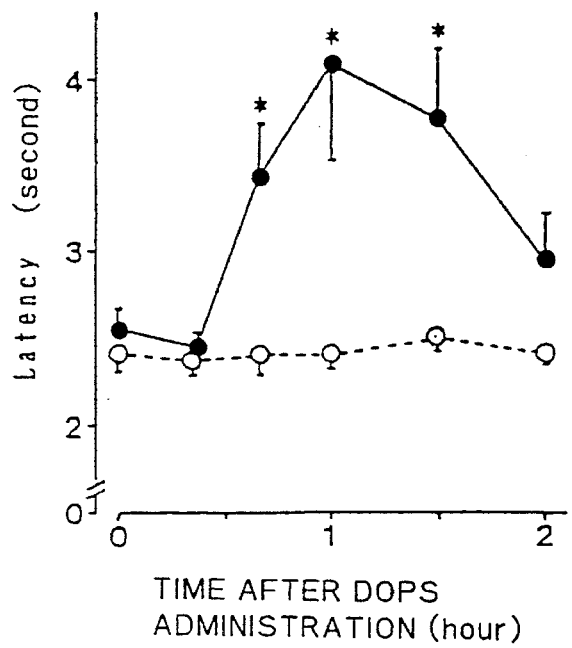
FIG. 1 shows the results of the analgesic effect of L-threo-DOPS assessed by the tail flick method.

Threo-DOPS used in the present invention is a known compound represented by the following formula:

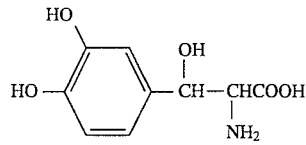

This compound may be prepared according to known methods as reported in Japanese Patent Application KOKOKU No. 1-49139 and U.S. Pat. No. 4,480,109. Threo-DOPS has optically active L- and D-forms and racemic DL-form. Among them, L-threo-DOPS is preferred for the purpose of the present invention. Since 1989, L-Threo-DOPS has been clinically applied to improve freezing gait observed in Parkinson's disease.

In the present invention, threo-DOPS may be employed also in the form of pharmaceutically acceptable acid addition salts thereof. To form the acid addition salts, there may be used inorganic acids such as hydrochloric acid, hydrobromic acid and sulfonic acid; and organic acids such as fumaric acid, citric acid, tartaric acid and succinic acid.

According to the present invention, threo-DOPS or its pharmaceutically acceptable acid addition salts may also be used in combination with a decarboxylase inhibitor. Preferred examples of such a decarboxylase inhibitor include benserazide and carbidopa.

It is known that, after administration, threo-DOPS is transported to a brain that is a site on which threo-DOPS acts, and then decarboxylated therein into a corresponding noradrenaline by decarboxylase to exhibit an activity for the treatment of Parkinson's disease (U.S. Pat. No. 4,497,826). It is also known that, where threo-DOPS is administered in combination with the decarboxylase inhibitor, decarboxylation of threo-DOPS by decarboxylase in the peripheral tissue can be prevented, resulting in that the transportation of threo-DOPS into a brain can be accelerated. As a result, a dose of threo-DOPS to be administered as a drug for treating Parkinson's disease may be reduced, and side effects of threo-DOPS in the peripheral tissue may be reduced (J. Pharm. Pharmacol., 1981, 33, 772–777).

As will be noted from test examples described hereinafter, threo-DOPS in the present invention is also considered to be transported into a brain and converted therein into noradrenaline to exhibit an analgesic effect. It is thus expected in the present invention that the combination of threo-DOPS with decarboxylase inhibitors will reduce a dose of threo-DOPS as an analgesic, and will therefore prevent side effects in the peripheral tissue.

Threo-DOPS or its pharmaceutically acceptable acid addition salt which is an effective ingredient of the present invention may be administered orally or parenterally at an appropriate dose in a conventional dosage form. Examples of preparations for oral administration include a tablet, capsule, syrup and suspension. Alternatively, threo-DOPS may also be administered parenterally in the dosage form of injection as a solution, emulsion or suspension.

The compositions suitable for administration may be prepared by mixing the effective ingredient with a pharmaceutically acceptable and conventionally used carrier, excipient, binder, stabilizer and the like. Where threo-DOPS is administered in the dosage form of an injection, the composition may be formulated with a pharmaceutically acceptable buffer, solution aid, isotonic solution and the like. As pointed out hereinbefore, threo-DOPS has already been provided for clinical use, and those preparations may be, therefore, used as they are.

Where threo-DOPS is administered in combination with a decarboxylase inhibitor, a kit comprising threo-DOPS or its pharmaceutically acceptable acid addition salt and a decarboxylase inhibitor is prepared and the thus prepared kit may be provided for such a combination administration.

A dose and dosage frequency of threo-DOPS or its pharmaceutically acceptable acid addition salt may vary depending upon the dosage form, conditions of disease to be treated, and the like. In the case of oral administration, the effective ingredient may be administered to adult in a daily dose of 0.1 to 3 g as a single dose or by dividing into several dosage frequency. A preferred mode of administration includes starting with oral administration to adult in a daily dose of 100 mg, increasing the dose depending upon necessity and determining the optimum dose to maintain a desired treatment. It is preferred to maintain the desired treatment by administering the effective ingredient in a standard dose of 600 mg daily at 3 dosage times per day.

Where a decarboxylase inhibitor is used in combination with the effective ingredient, it is sufficient to administer the inhibitor in a dose less than the dose of threo-DOPS by about $\frac{1}{10}$.

Threo-DOPS has an extremely weak toxicity, that is, $LD_{50}$ is 10 g/kg or more when orally administered to mouse, and about 10 g/kg when intraperitoreally admnised to mouse. It would be believed that no substantially adverse effects are caused, when the effective ingredient is administered within the effective dose which is required for the present invention.

The analgesic composition of the present invention is effective for treating pains such as postoperative pain, headache, migraine, pains accompanied by rheumatism, postherpes neuralgia, cancerous pain, pains associated with cervico-omo-brachial syndrome, shoulder periarthritis, spinal distortion, and spondylosis deformans.

That is, it has been confirmed that the analgesic composition of the present invention comprising threo-DOPS as an effective ingredient has the effects set forth below, as will be noted from test examples hereinafter.

(1) Effect Against Acute Pain

Thermal stimulation at a certain level was given onto mice at the tail, and the latency until the animal flicked the tail out of the thermal stimulation was measured. The analgesic effect was judged in terms of prolonged latency by administration of a drug (tail-flick test, see European Journal of Pharmacology, 212, 1992). The tail-flick test reveals that threo-DOPS exhibits the analgesic effect dose-dependently when subcutaneously administered to mice.

(2) Effect Against Chronic Pain

Mice were used for the kaolin-induced writhing test and the formalin test, wherein animal model for assessment of chronic pain is used [Pain, 51, 195–198 (1992)]. The analgesic effect was dose- dependently observed when threo-DOPS was administered subcutaneously and orally.

(3) Mechanism of the Analgesic Effect of Threo-DOPS

The analgesic effect of threo-DOPS is non-narcotic, because the effect was not antagonized by morphine antagonist, naloxone. Furthermore, the analgesic effect of threo-DOPS was suppressed by the administration of an adrenaline blocker, phentolamine, in the brain, and thus shown to act via adrenergic nerve in the brain. Such pharmacological properties of threo-DOPS are quite dissimilar to those of conventional analgesics.

These results reveal that threo-DOPS or pharmaceutically acceptable acid addition salt thereof used in the present invention have a mechanism different from that of known analgesics, suggesting that the analgesics of the present invention would be effective not only for acute pain but also for chronic pain.

The effects of the present invention are made clearer below, by referring to the following test examples.

Test Example 1

Antinociceptive tests for L-threo-DOPS a) Tail Flick Test

Method

The test was conducted by using a tail flick analgesia meter (MK-330, Muromachi Kikai). The intensity of the beam was adjusted to produce a control latency of 2 to 2.5 seconds, and a cut-off time was set to be 8 seconds. The experimental data obtained were shown in terms of latency (second).

L-Threo-DOPS was suspended in a 0.2% Tween 80 solution and the resulting suspension was subcutaneously administered in a dose of 100 to 400 mg/kg. The tail flick latency was then measured with passage of time to determine antinociceptive action, namely, analgesic activity.

Results

Figure 1B:
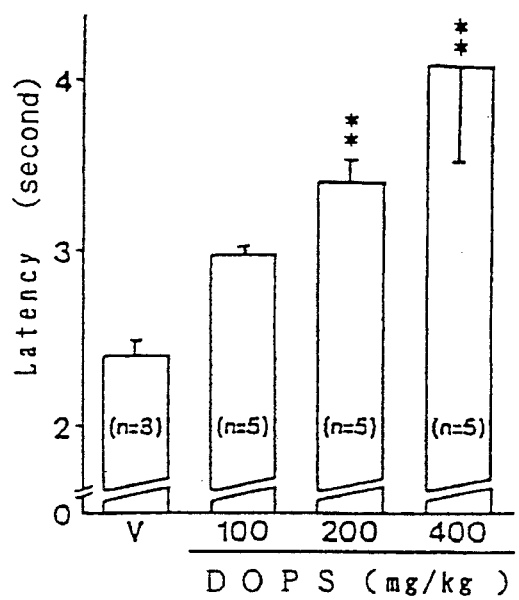

The results are shown in FIG. 1. The left graph in FIG. 1 shows latency with passage of time after subcutaneous administration of L-threo-DOPS in a dose of 400 mg/kg according to the tail flick test. In the left graph, the symbol ○ denotes the group administered with vehicle only (n=8), and the symbol ● denotes the group administered with L-threo-DOPS (n=5). The right graph in FIG. 1 shows a relationship between the dose of L-threo-DOPS administered and latency (second) one hour after administration of L-threo-DOPS. In the right graph, the symbol V denotes the group administered with vehicle only. *$P<0.05$, **$P<0.01$ (when compared to the group administered with vehicle only).

As is seen from FIG. 1, 40 or more minutes after administration of L-threo-DOPS in a dose of 400 mg/kg, a significantly prolonged latency was observed, and reached the maximum latency one hour after. Thereafter, the latency was gradually recovered, and no significant effect was observed 2 hours later (see the left graph). The antinociceptive action of L-threo-DOPS, 60 minutes after administration, was dose-dependent in the range of 100 to 400 mg/kg (see the right graph).

b) Kaolin-Induced Writhing Test

Method

The test was proposed by Fujiyoshi, T. et al. as a nociceptive test for the assessment of endogenous bradykinin-induced pain [Fujiyoshi et al., Agents and Actions, 27, 332

(1989)]. In the present invention, a method somewhat modified from the Fujiyoshi test was used for the assessment. That is, a suspension of 125 mg/kg of kaolin in 0.2% Tween 80 solution was intraperitoneally administered to mice in a dose of 0.25 ml/10 g. Immediately thereafter, the total number of writhing reactions which were observed during 20 minutes was counted.

Thirty minutes, 1 hour and 2 hours before administration of kaolin, L-threo-DOPS was subcutaneously administered in a dose ranging from 100 to 400 mg/kg.

Results

Figure 2A:
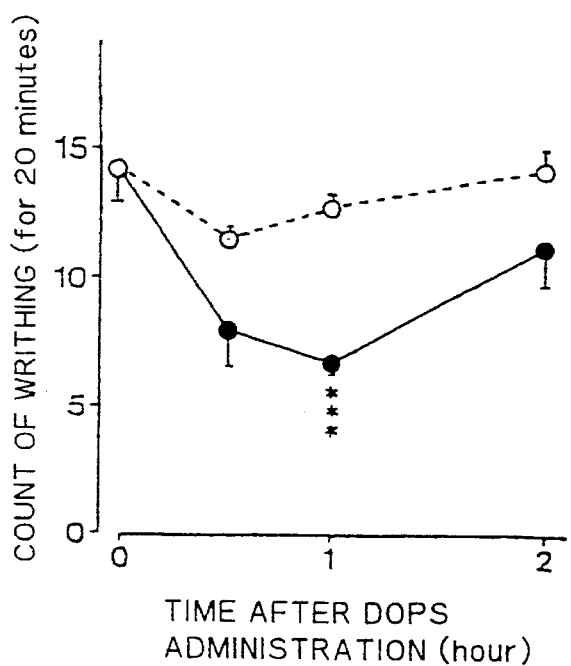
FIG. 2 shows the results of the analgesic effect of L-threo-DOPS assessed by the kaolin-induced writhing test.
Figure 2B:
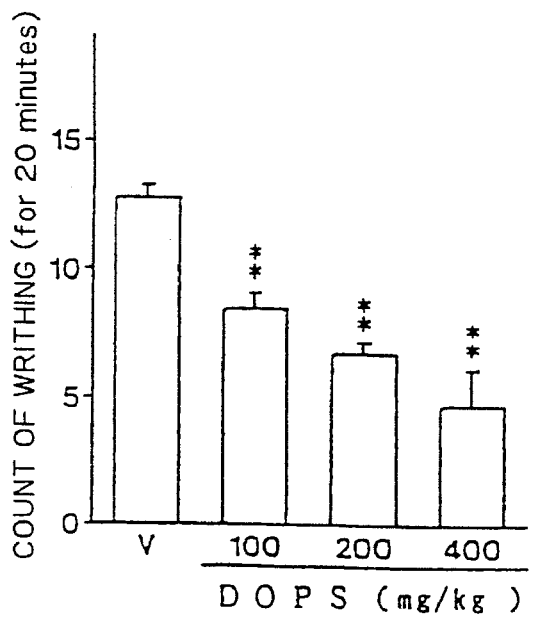

The results are shown in FIG. 2. The left graph in FIG. 2 shows the total count of writhing reactions with passage of time, after L-threo-DOPS was subcutaneously administered in a dose of 200 mg/kg according to the kaolin-induced writhing method. In the left graph, the symbol ○ denotes the group administered with vehicle only, and the symbol ● denotes the group administered with L-threo-DOPS. The right graph in FIG. 2 shows a relationship between the dose of L-threo-DOPS administered and the total count of writhing reactions one hour after administration of L-threo-DOPS. The symbol V denotes the group administered with vehicle only (n=5). $P<0.01$, *$P<0.001$ (when compared to the group administered with vehicle only).

As is seen from FIG. 2, after administration of L-threo-DOPS in a dose of 200 mg/kg, the count of kaolin-induced writhing response decreased to the half, indicating a significant antinociceptive action. The decreasing tendency was also observed 30 minutes and 2 hours after administration of L-threo-DOPS, but the observed decrease was insignificant (see the left graph). The effect which was observed 60 minutes after administration of L-threo-DOPS was dose-dependent in the range of 100 to 400 mg/kg (see the right graph).

c) Formalin-Induced Nociceptive Test

Method

Formalin (0.5%, 25 μl) was administered subcutaneously into a mouse at the sole of the right hind paw. Immediately thereafter, the time required for the mouse to conduct licking or biting behavior was counted for 30 minutes at intervals of 5 minutes. The results are shown separately for Phase I (0–5 minutes after the formalin administration) and Phase II (10–30 minutes after the formalin administration).

Fifty minutes before the formalin administration, L-threo-DOPS was subcutaneously administered in a dose ranging from 100 to 200 mg/kg.

Results

The results are shown in FIG. 3. The left graph in FIG. 3 shows in the formalin-induced nociceptive test a relationship between the times required for licking and biting (second) for Phase I (0–5 minutes after the formalin administration) and the dose of L-threo-DOPS administered. The right graph in FIG. 3 shows in the formalin-induced nociceptive test (n=9–11) a relationship between the times required for licking and biting (second) for Phase II (10–30 minutes after the formalin administration) and the dose of L-threo-DOPS administered. The symbol V denotes the group administered with vehicle only. *$P<0.05$ (as compared to the group administered with vehicle only).

As is seen from FIG. 3, subcutaneous administration of L-threo-DOPS in a dose of 100 to 200 mg/kg did not affect the time required for the nociceptive reaction for Phase I (the left graph), but dose-dependently inhibited the reaction for Phase II (the right graph). While not shown in the graphs, even though the dose of L-threo-DOPS was increased to 400 mg/kg, no better effect was obtained.

The results obtained in the respective tests are all shown by means ±standard error. Statistically significant difference between the groups was determined by Student's t-test or Newman-Keuls test. When $P<0.05$, the difference was judged to be significant.

Test Example 2

Antagonistic Effect of L-threo-DOPS Antinociceptive Action on Naloxone (Morphine Antagonist)

Method

Tests were conducted in the same way as the tail flick test method and the kaolin-induced writhing test method in Test Example 1 described above. In the tail flick test method, however, 1 mg/kg of naloxone was subcutaneously administered 40 minutes after administration of 400 mg/kg of L-threo-DOPS, and the latency was measured 60 minutes after the 400 mg/kg L-threo-DOPS administration. The obtained data are shown in terms of change in latency (Δ latency). In the kaolin-induced writhing test, 0.01 mg/kg of naloxone was subcutaneously administered 55 minutes after administration of 400 mg/kg of L-threo-DOPS, and kaolin was administered 5 minutes after the administration of naloxone.

The results obtained in the tests are all shown by means ±standard error. Statistically significant difference between the groups was determined by Student's t-test or Newman-Keuls test. When $P<0.05$, the difference was judged to be significant.

Results

Figure 4A:
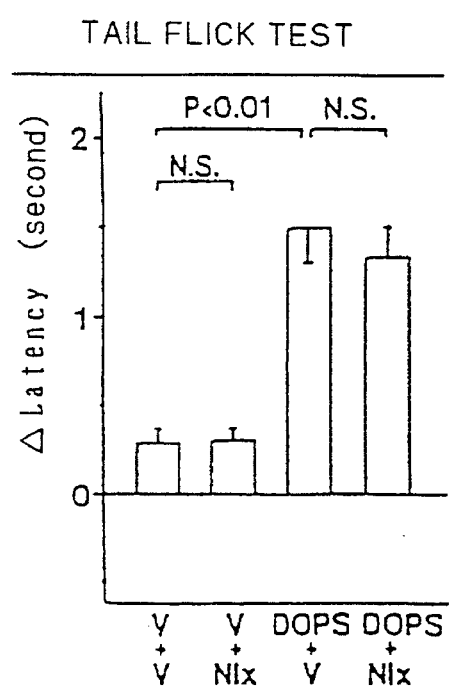
FIG. 4 shows the results of morphine antagonist, naloxone, on the analgesic effect of L-threo-DOPS assessed by the tail flick method and the kaolin-induced writhing test.
Figure 4B:
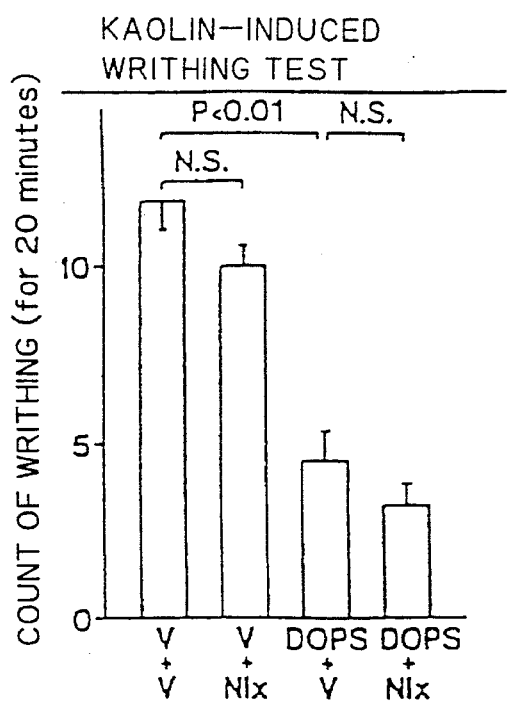

The results are shown in FIG. 4. The left graph in FIG. 4 shows change in latency (Δ latency (second)) 60 minutes after administration of L-threo-DOPS according to the tail flick method (n=1). The right graph in FIG. 4 shows the total count of writhing reactions 60 minutes after administration of L-threo-DOPS according to the kaolin-induced writhing test (n=4 or 5). The symbol V denotes the group administered with vehicle only, and the symbol N.S. denotes that there is no significant difference as compared to the control group.

As is seen from FIG. 4, the antinociceptive action of L-threo-DOPS in the tail flick test and the kaolin-induced writhing test was hardly affected by morphine antagonist, naloxone (Nlx). This reveals that the action of L-threo-DOPS is non-narcotic analgesic activity.

Test Example 3

Effect of Phentolamine as an α-Adrenaline Receptor Blocker on the Antinociceptive Action of L-threo-DOPS Method Phentolamine was administered intracerebral-ventricularly (i.c.v.) or intrathecaly (i.th.) in a dose of 0.1 to 1 μg/mouse, 40 minutes after L-threo-DOPS was administered in a dose of 400 mg/kg. Then, the effect of phentolamine against L-threo-DOPS-induced antinociceptive action was determined in the tail flick test.

The results obtained in the test are all shown by means ±standard error. Statistically significant difference between the groups was determined by Student's t-test or Newman-Keuls test. When $P<0.05$, the difference was judged to be significant.

Results

Figure 5A:
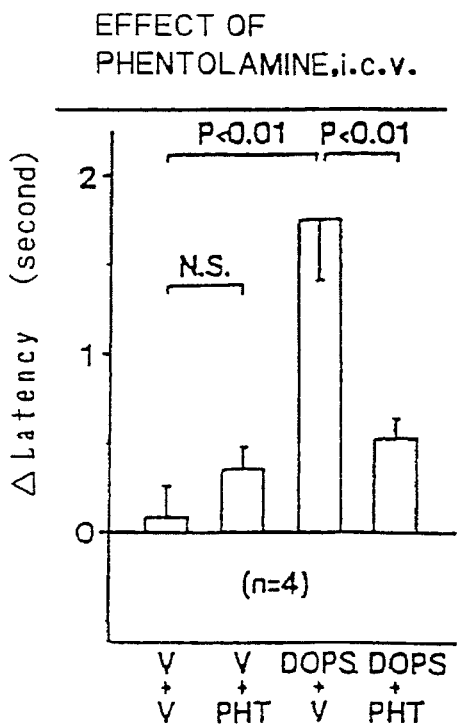
FIG. 5 shows the results of adrenaline blocking agent, phentolamine, on the analgesic effect of L-threo-DOPS assessed by the tail flick method.
Figure 5B:
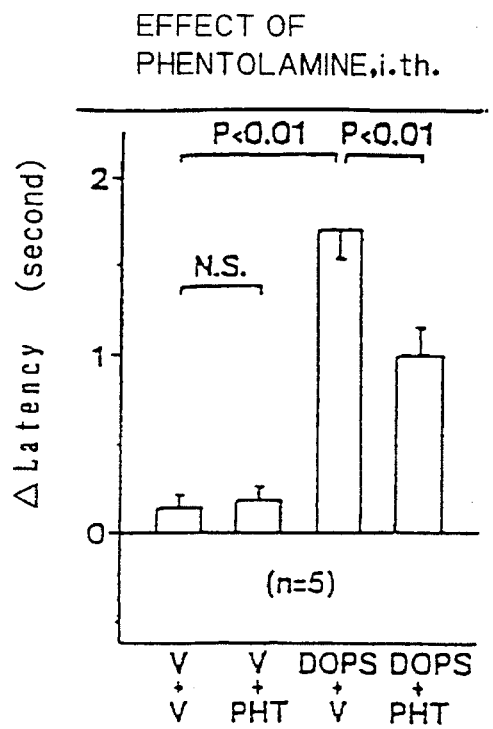

The results are shown in FIG. 5. The results in FIG. 5 indicates change in latency (Δ latency, second) 60 minutes after the L-threo-DOPS administration. The left graph in FIG. 5 shows the effect of phentolamine when intracerebralventricularly (i.c.v.) administered, and the right graph in FIG. 5 shows the effect of phentolamine when intrathecaly (i.th.) administered. The symbol V denotes the group administered with vehicle only, and the symbol N.S. denotes that there is no significant difference as compared to the control group.

As is seen from FIG. 5, when phentolamine (PHT) as an α-adrenaline receptor blocker was intracerebralventricularly administered in a dose of 1 µg/mouse, phentolamine itself did not affect the latency. However, phentolamine almost completely inhibited prolongation of the latency by subcutaneous administration of L-threo-DOPS in a dose of 400 mg/kg (see the left graph). This effect by phentolamine was also observed even at a reduced dose of 0.1 µg/mouse. On the other hand, when phentolamine was intracerebralventricularly administered in a dose of 1 µg/mouse, the antinociceptive action of L-threo-DOPS (400 mg/kg, s.c.) was partially but significantly inhibited (see the right graph).

The results shown in Test Examples 1 through 3 reveal that L-threo-DOPS exhibits a non-opiate type antinociceptive action by systemic administration. It is also suggested that noradrenergic system in the brain and spinal code would be involved in the antinociceptive action.

Test Example 4

Effect of Benserazide (Peripheral Nerve Decarboxylase Inhibitor) on the Antinociceptive Action of L-threo-DOPS Method Benserazide was administered subcutaneously in a dose of 1 mg/kg, 60 minutes before the subcutainious administration of L-threo-DOPS (400 mg/kg). Alternatively, benserazide was administered intracerebralventricularly at a dose of 25 µg/mouse, 30 minutes before L-threo-DOPS was subcutaneously administered in a dose of 400 mg/kg. The effect of benserazide on the L-threo-DOPS-induced antinociceptive action 60 minutes after the L-threo-DOPS administration was examined according to the tail flick test.

The results obtained in this test are all shown by means ±standard error. Statistically significant difference between the groups was determined by Student's t-test or Newman-Keuls test. When P<0.05, the difference was judged to be significant.

Results

The results are shown in FIG. 6. The results in FIG. 6 indicate change in latency (Δ latency, second) 60 minutes after the L-threo-DOPS administration. The left graph in FIG. 6 shows the effect of benserazide when subcutaneously administered, and the right graph in FIG. 5 shows the effect of benserazide when administered intracerebralventricularly. The symbol V denotes the group administered with vehicle only, and the symbol N.S. denotes that there is no significant difference as compared to the control group.

As is seen from FIG. 6, when benserazide (BSZ) as a peripheral decarboxylase inhibitor was administered subcutaneously, BSZ did not give any significant effect on the antinociceptive action of L-threo-DOPS (see the left graph). However, when benserazide was administered intracerebralventricularly, the antinociceptive action of L-threo-DOPS was potently inhibited (see the right graph).

The forgoing results suggest that L-threo-DOPS would be transported into the central nervous system (brain and spinal code) after systemic administration, and decarboxylated therein by decarboxylase into noradrenaline to exhibit an antinociceptive activity.

Test Example 5

Antinociceptive Action of L-threo-DOPS by Oral Administration

Method

L-Threo-DOPS was orally administered to mice in doses of 200, 400 and 800 mg/kg, and was examined for the antinociceptive action according to the tail flick test method.

The results obtained in this test are all shown by means ±standard error. Statistically significant difference between the groups was determined by Student's t-test or Newman-Keuls test. When P<0.05, the difference was judged to be significant.

Results

Figure 7:
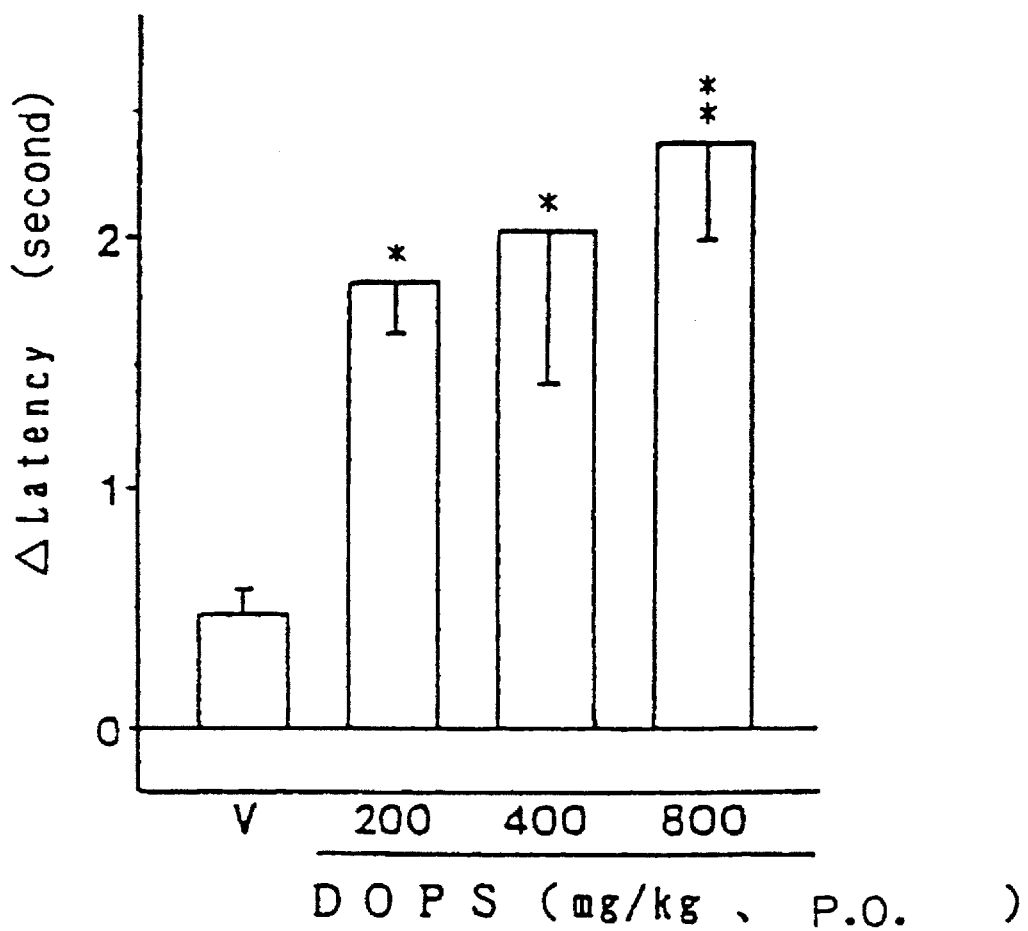
FIG. 7 shows the results of the analgesic effect of L-threo-DOPS by oral administration, which was assessed by the tail flick method.

The results are shown in FIG. 7. The results in FIG. 7 indicate, in the tail flick test, a relationship between the dose of L-threo-DOPS when orally administered and change in latency (Δ latency, second) 60 minutes after the L-threo-DOPS administration (n=6). *P<0.05, **P<0.01 (as compared to the control group).

As is seen from FIG. 7, L-threo-DOPS shows the antinociceptive action dose-dependently when orally administered in the range of 200 to 800 mg/kg. In all cases, a significant effect was observed 40 or more minutes after the administration, and reached the maximum level 60 minutes after the administration. Then, the effect gradually decreased. The results establish that L-threo-DOPS is also effective when orally administered.

Hereinafter, the pharmaceutical formulation of the present invention is described below in detail, with reference to the following examples.

EXAMPLE 1

Preparation of Capsule

Two hundreds parts by weight of L-threo-DOPS, 167 parts by weight of excipient and 3 parts by weight of lubricant are uniformly mixed with each other. The mixture is then filled up in empty capsules to prepare capsules containing 200 mg of L-threo-DOPS.

EXAMPLE 2

Preparation of Capsule

Hundred parts by weight of L-threo-DOPS, 168 parts by weight of excipient and 2 parts by weight of lubricant are uniformly mixed with each other. The mixture is then filled up in empty capsules to prepare capsules containing 100 mg of L-threo-DOPS.

The excipient used in Examples 1 and 2 described above is selected from lactose, refined sugar, glucose, D-mannitol, potato starch, corn starch, wheat starch, calcium carbonate, calcium sulfate, anhydrous calcium phosphate, sodium hydrogencarbonate, crystalline cellulose and a mixture thereof. The lubricant used above is selected from magnesium stearate, calcium stearate, talc and the like.

Industrial Utility

According to the present invention, it has been revealed that threo-DOPS exhibits an analgesic activity which is effective for acute pains and chronic or continuous pains. Therefore, threo-DOPS is extremely effective for the treatment of diseases with pains such as postoperative pain, headache, migraine, pains accompanied by rheumatism, post-herpes neuralgia, cancerous pain, pains associated with cervico-omo-brachial syndrome, shoulder periarthritis, spinal distortion, and spondylosis deformans.

I claim:

1. A method for the treatment of pain which comprises administering to a human an effective dose of threo-3-(3,4-dihydroxyphenyl)serine or a pharmaceutically acceptable acid addition salt thereof.

2. The method according to claim 1, wherein threo-3-(3,4-dihydroxyphenyl)serine or a pharmaceutically acceptable acid addition salt thereof is administered in combination with at least one decarboxylase inhibitor selected from benserazide and carbidopa.

3. The method according to claim 1, wherein the pain is chronic pain.

4. The method according to claim 1, wherein said threo-3-(3,4-dihydroxyphenyl) serine is in the L-form.

* * * * *